United States Patent
Lenaerts et al.

(10) Patent No.: US 6,284,273 B1
(45) Date of Patent: *Sep. 4, 2001

(54) CROSS-LINKED HIGH AMYLOSE STARCH RESISTANT TO AMYLASE AS A MATRIX FOR THE SLOW RELEASE OF BIOLOGICALLY ACTIVE COMPOUNDS

(76) Inventors: Vincent Lenaerts, 77 Holton Avenue, Westmount, P.Q. (CA), H3Y 2G1; Francois Chouinard, 14 Ch. D'Agremont, Lorraine (CA), J62 4E4; Mircea Alexandru Mateescu, 377 Sherbrooke Street West, Apt. 505, Montreal, PQ (CA), H3A 1B5; Pompilia Ispas-Szabo, 3250 Forest Hill, Montreal, PQ (CA), H3V 1C8

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 75 days.

(21) Appl. No.: 09/028,385

(22) Filed: Feb. 24, 1998

(51) Int. Cl.[7] .............................. A61K 9/44; A61K 9/26; A61K 47/00

(52) U.S. Cl. ........................ 424/468; 424/469; 424/470; 514/777

(58) Field of Search ................................. 424/488, 489, 424/464, 465, 497, 486, 469, 470; 514/160

(56) References Cited

U.S. PATENT DOCUMENTS 5,830,884 * 11/1998 Kasica et al. ..................... 514/160

\* cited by examiner

*Primary Examiner*—Thurman K. Page
*Assistant Examiner*—Blessing Fubara
(74) *Attorney, Agent, or Firm*—Pennie & Edmonds LLP

(57) ABSTRACT

The present invention is concerned with a solid slow release oral pharmaceutical dosage unit resistant to amylase which comprises a solid dosage unit made up of an admixture of a therapeutic dosage of an orally effective pharmaceutical product, an optional polysaccharide or polyol, and cross-linked high amylose starch, wherein the cross-linking of the high amylose starch has been carried out with a covalent or non-covalent cross-linking agent with from about 0.1 g to about 30 g of cross-linking agent per 100 g of high amylose starch.

34 Claims, 2 Drawing Sheets

CROSS-LINKED HIGH AMYLOSE STARCH RESISTANT TO AMYLASE AS A MATRIX FOR THE SLOW RELEASE OF BIOLOGICALLY ACTIVE COMPOUNDS

FIELD OF THE INVENTION

The present invention relates to a slow release pharmaceutical tablet, and more particularly to a slow release pharmaceutical tablet incorporating a covalent or non-covalent cross-linked polymer of a mixture of amylose and amylopectin as the slow release matrix.

PRIOR ART

The controlled release of biactive molecules has been the subject of extensive research over the last half of the twentieth century. The controlled release of some drugs is of high importance for biopharmaceutical applications. Long acting doses of a variety of drugs are now available, allowing once or twice-a-day dosage regimens where immediate release forms called for multiple and sometimes impractical administrations. Effective slow-release dosage regimens have demonstrated superior patient compliance and hence improved efficacy over multiple immediate release forms.

There are several types of polymers which have already been used as a matrix for the slow-release of drugs. Thus, polymeric materials such as polyvinyl chloride, polyethylene polyamides, ethylcellulose, silicone, poly (hydroxyethyl methacrylate), other acrylic co-polymers, polyvinylacetate-polyvinyl chloride copolymers and other polymers were described as an adequate matrix for tablet preparation (see for example U.S. Pat. No. 3,087,860; U.S. Pat. No. 2,987,445; and Pharm. Acta Helv., 1980, 55, 174–182, Salomon et al.).

Polysaccharides have been used widely in pharmaceutical, chemical, and biochemical drug delivery. This family of natural polymers has been applied to the area of controlled release coatings, matrices, macromolecular carriers and biodegradable carriers. One of the most frequent problems associated with the use of polysaccharides, such as starch, as drug delivery agents is the susceptibility to degradation by intestinal polysaccharidases such a $\alpha$-amylase. The use of polysaccharides in colonic drug delivery has been reviewed (Critical Reviews™ in Therapeutic Drug Carrier Systems, 13 (3 & 4):185–223 (1996).

Starch is, however, one of the most attractive biopolymers for use as a drug delivery agent since it can be mass produced with a high purity at a very economical price. Recently, in order to apply amylose to the controlled release field, a chemically modified amylose was prepared by cross-linking amylose in the gelatinized state as described in U.S. Pat. No. 5,456,921.

Amylose is a natural substance obtained from starch. It is essentially a linear, non-branched, polymer of glucopyranose units with $\alpha$-D-(1–4) linkages. In starch, amylose is usually accompanied by amylopectin, which is a branched polyglucose polymer with a significant frequency of branching points based on $\alpha$-(1–6)-glucosidic bonds. Cross-linked amylose (CLAm) is a novel excipient for the controlled release of drugs in solid drug dosage forms. CLAm is produced by the reaction of amylose with a suitable cross-linking agent in an alkaline medium. Different degrees of cross-linking (CLAx) can be obtained by varying the ratio of cross-linking agent, such as epichlorohydrin, to amylose in the reaction vessel where n indicates the amount (g) of cross-linking agent used for cross-linking 100 g of amylose (i.e., CLAx with x=0, 6, 11, 15 or 30).

CLAm tablets are prepared by direct compression and are highly resistant to mechanical stress in the dry state. When in contact with aqueous fluids, water diffuses into the matrix with subsequent formation of a gel layer. Progressive water sorption leads to significant swelling of the matrix. With degrees of cross-linking below 11, the swollen polymeric matrix does not undergo any erosion in vitro resulting in a dense and homogeneous rubbery matrix. The in vitro medium does not contain any amylase.

Cross-linked amylose (CLAm) has been used as a controlled release (CR) matrix for tablets. However, in certain formulations, tablets were not resistant to amylase, an enzyme responsible for the metabolism of amylose in the human intestine. As a result, tablets containing cross-linked amylose are not resistant to amylase attack and accelerated dose release can occur in vivo or in the presence of enzymes instead of controlled release.

Another feature of cross-linked amylose is its ability to release drugs at a constant rate, following zero-order kinetics, such as described in S.T.P. Pharma 1986, 2, 38–46 (Peppas et al.). The approach called 'swelling-controlled' systems consists of glassy polymers into which a water front penetrates at a constant rate. Behind this front, the polymer is in a rubbery state. Provided the drug diffusion coefficient in the rubbery polymer is much higher than in the glassy polymer, a zero order release can be achieved to a certain degree. However, the delivery rate is constant only for a limited fraction of the release, usually around 60% of the total amount of contained drug, and requires a low initial drug concentration.

X-ray diffraction studies show different morphologic forms for amylose in correlation with its origin, preparation mode or hydration state (French D. 25—"Organization of starch granules"—in Starch: Chemistry and Technology [Whistler R., L., BeMiller J., N. and Paschall E. F., Eds.], Acad. Press, 1984). The structures of A and B-type amylose are based on double helices parallel stranded and antiparallel packed, the individual strands being in a right-handed six-fold helical conformation (Wu H. C. and Sarko A., Carbohydr. Res., 61, 7–25, 1978). Amylose A contains 8 molecules of $H_2O$ and Amylose B (hydrated) contains 36 molecules of $H_2O$ per elementary cell unit. V-Amylose is made from single helix chains and exists as complexes with small organic molecules, water or iodine. Even though the inside of the helix channel of V-Amyloses is primarily hydrophobic, intrahelical water has been found in anhydrous (Va), as well as in the hydrated (Vh) forms. Some intermolecular hydrogen bonds are formed through interstitial water molecules. It has been suggested that the presence of a substantial amount of complexing agent (e.g., ethanol) can mainly stabilize single helices of amylose, whereas a predominance of water can induce conformational changes leading to the formation of double helices (Buleon A., Duprat F., Booy F. P. and Chanzy H., Carbohydr. Polymer, 4 161–173, 1984). All forms of amylose become B-type in gel phase (Wu H. C. and Sarko A., Carbohydr. Res., 61, 27–40, 1978); the interchange of morphological structures tends to reach the more stable double helix form with the corresponding molecules of water.

Accordingly, it would be desirable to provide a slow release system following a zero-order kinetics, and allowing a controlled release of a drug at a constant rate until all the drug is released, whatever the concentration of the drug in the system.

Suitable covalent cross-linking agents are 2,3-dibromopropanol, epichlorohydrin, sodium trimetaphosphate, linear mixed anhydrides of acetic and di- or tribasic carboxylic acids, vinyl sulfone, diepoxides, cyanuric chloride, hexahydro-1,3,5-trisacryloyl-s-triazine, hexamethylene diisocyanate, toluene 2,4-diisocyanate, N,N-methylenebisacrylamide, N,N'-bis(hydroxymethyl) ethyleneurea, phosgene, tripolyphosphate, mixed carbonic-carboxylic acid anhydrides, imidazolides of carbonic and polybasic carboxylic acids, imidazolium salts of polybasic carboxylic acids, guanidine derivatives of polycarboxylic acids, and esters of propanoic acid.

Suitable agents that could be used as additives to high amylose starch for controlled release prior to cross-linking of the high amylose starch include, but are not limited to, polyvinyl alcohol, β-(1–3) xylan, xanthan gum, locust bean gum and guar gum.

SUMMARY OF THE INVENTION

In accordance with the present invention there is now provided a solid slow release oral pharmaceutical dosage unit which comprises a solid dosage unit made up of an admixture of a therapeutic dosage of an orally effective pharmaceutical product and covalent cross-linked polymer of high amylose starch made by reacting high amylose starch with a suitable cross-linking agent, wherein the covalent cross-linking of the polymer has been carried out with from about 0.1 to about 30 g of cross-linking agent per 100 g of amylose.

In a further aspect of the invention, there is provided a solid slow release oral pharmaceutical dosage unit made up of an admixture of a therapeutic dosage of an orally effective pharmaceutical product, an optional polysaccharide or polyol and a cross-linked polymer of high amylose starch made by reacting high amylose starch with a suitable cross-linking agent.

In another aspect of the invention, the pharmaceutical product is present in the tablet in an amount of from 0.01 to 80% w/w.

In a further aspect of the invention, a method is described to obtain a matrix resistant to all types of amylase, obviating the concern over premature degradation of the tablet and accelerated release of the orally effective pharmaceutical product.

DETAILED DESCRIPTION OF THE INVENTION

The cross-linking of amylose is well known in the literature. For example, the desired cross-linking can be carried out in the manner described in BIOCHMIE 1978, 60, 535–537 (Mateescu) by reacting amylose with epichlorohydrin in an alkaline medium. In the same manner, amylose can also be cross-linked with 2,3-dibromopropanol, sodium trimetaphosphate and other suitable cross-linking agents described herein.

Essentially, the high amylose starch is swollen in water by generally known gelatinization techniques such as alkaline or heat treatment and after homogenization, an appropriate amount of cross-linking agent is added. After substantial homogenization, the reaction medium is transferred onto a water bath and heated for one hour at a temperature of from 40° to 45° C. and the temperature is then raised from 60° to 75° C. for a further period of from 1 to 2 hours after which time the reaction is complete. The duration of heating can be varied as well as the amount of cross-linking agent used in the reaction.

The resulting cross-linked material is then sieved in wet form and the granules ranging from about 25 to about 700 um are collected for the preparation of the slow-release tablet of the present invention. The granules of 25 to about 300 um representing at least 50% of the granules are selected for use in accordance with the presented invention.

The preferred cross-linked polymers of high amylose starch with covalent cross-linking agents suitable for the purposes of the present invention are those where from about 0.1 to about 30 g of covalent cross-linking agent have been used to cross-link 100 g of high amylose starch. More preferred cross-linked polymers were obtained when from about 0.5 g to about 6.0 g of covalent cross-linking agents over 100 g of high amylose starch were used.

It has been surprisingly found that when a mixture of amylose and amylopectin between about 10–60% amylopectin by weight is cross-linked by a covalent cross-linking agent comprising sodium trimetaphosphate, 2,3-dibromopropanol, epichlorohydrin, and epibromohydrin or mixed with a suitable polysaccharide or polyol are compressed into tablets, those tablets are resistant to amylase degradation provided that the lubricant used for tableting is not magnesium stearate. These tablets can then be used for the controlled release of oral pharmaceutical products. Conversely, when the objects of the invention are dispersed as a powder in an amylase medium, they are readily degraded. Therefore, when placed in a tablet, it was entirely unexpected that the objects of the invention were stable to amylase.

It has also been surprisingly found that when covalently cross-linked high amylose starch of the invention is exposed to water, it predominantly forms a double helix similar to the B-form of amylose. Upon placement of a high amylose cross-linked starch tablet in water, a gel is formed very quickly at the polymer surface. As the progression of the gel front toward the center of the tablet ceases rapidly, water diffuses into the polymer and reaches the center in about 30 min. As water continues to penetrate, the water gradient in the core progressively diminishes and the core expands, mainly radially. This process goes on for several hours, until the core turns into a gel and equilibrium swelling is reached. In the gel state, the cross-linked high amylose starch, which was initially arranged mainly in the amorphous state and in V type single helices, progressively adopts the B-type double helices conformation, forming a three-dimensional physical network over a long distance. Both amylose and PVA can adopt helical confirmations. PVA is an interesting polymer with alternating hydrophilic (CHOH) and hydrophobic ($CH_2$) groups, and consequently, undergoes lower swelling in water than amylose.

The present invention will be more readily understood by referring to the following examples which are given to illustrate the invention rather than limit its scope.

DESCRIPTION OF THE FIGURES

FIGS. I and II illustrate the release characteristics of pure cross-linked high amylose starch tablets containing acetaminophen and pseudoephedrine, respectively. The data indicate that the tablets are not sensitive to enzymatic degradation by amylase. The specific type of amylose used in these examples contained at least 20% amylopectin and was cross-linked with sodium trimetaphosphate.

EXPERIMENTAL

Materials and Methods

Materials

Figure 1:
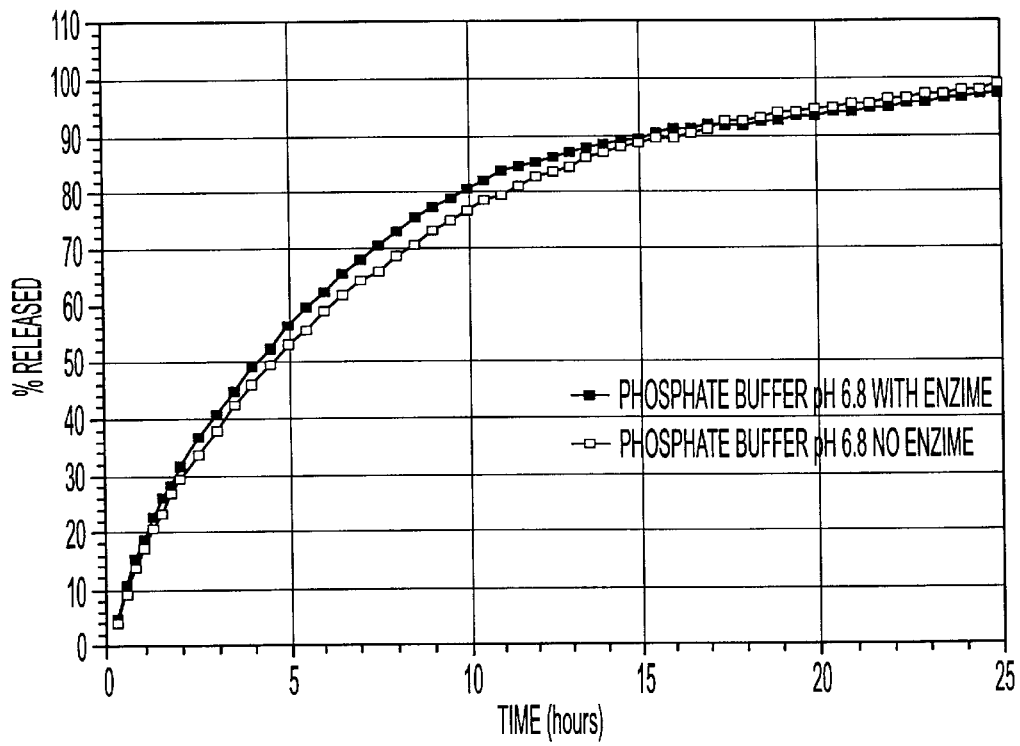
Figure 2:
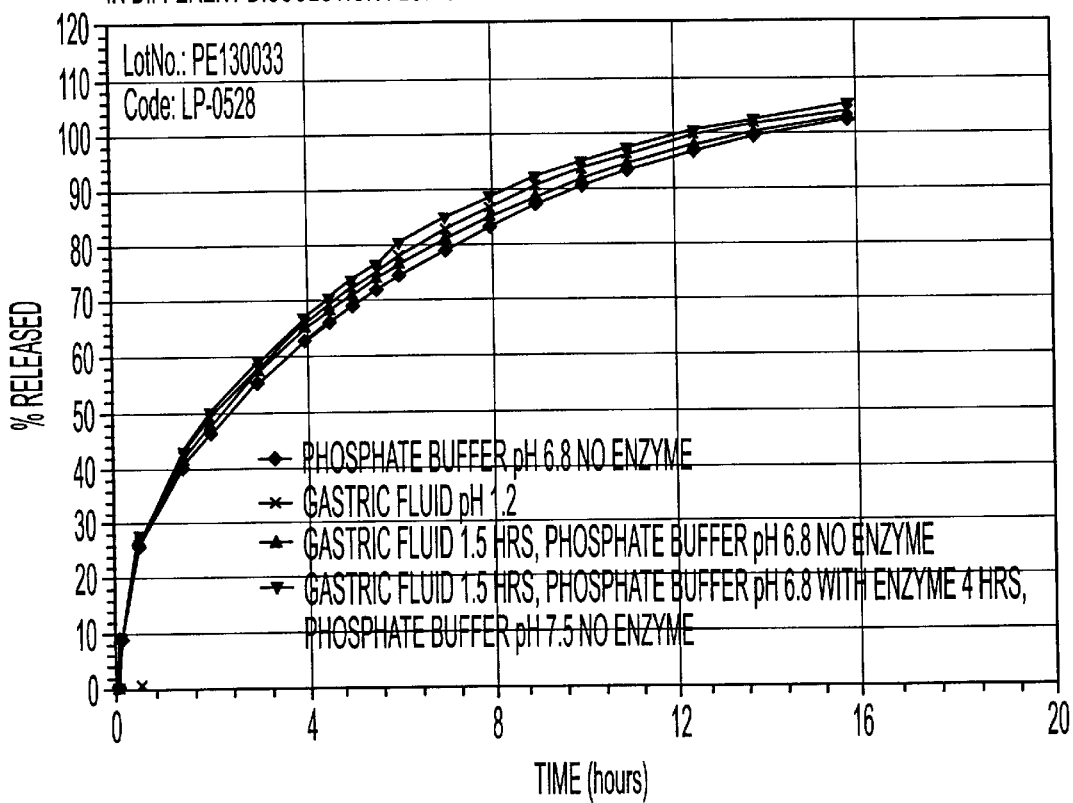

High Amylose Starch: Hylon VII powder purchased from National Starch (A);

PVA powders (Aldrich) with different molecular masses (9000–146000 Da), and 80–89% hydrolysis degree (Hydrolysis degree is the number of acetate groups left after hydrolysis of polyvinyl-acetate (PVAc) to generate PVA, calculated in percentage from the initial number of acetate functional groups);

Epichlorohydrin, sodium trimetaphosphate (Sigma Chem Co.),

α-amylase (EC 3.2.1.1) from Bacillus species from Sigma Chemical Co., acetic acid glacial, monobasic and dibasic sodium phosphate (from Anachemia);

NaOH and acetone (ACS quality);

A. Synthesis of Cross-Linked Polymers-Cross-Linked High Amylose Starch (CLA), and Co-Cross-Linked High Amylose Starch-PVA A.1. Synthesis of Cross-linked High Amylose Starch (CLA-0, CLA-3, CLA-6, CLA-8 and CLA-14)

For each synthesis, a quantity of 300 g of high amylose starch powder and a volume of 1.75 L of 0.85 N sodium hydroxide (55° C.) were mixed in a Hobart® planetary mixer tank N-50, maintaining the temperature at 50° C. for gelatinization. After 20 minutes of homogenization, a volume of 0 mL, 7.60 mL, 15.24 mL, 20.30 mL or 38.10 mL of epichlorohydrin (corresponding to the required cross-linking degree) was respectively added in each synthesis batch. For instance, for CLA-6 a volume of 15.24 mL of epichlorohydrin corresponding to 18 g (d=1.19 g/mL) was added. Each reaction mixture was again homogenized for 20 minutes. The reaction was continued for a period up to 1 h, under moderate heating (40–70° C.). The mixture was neutralized with acetic acid, and then thoroughly washed on a Buchner funnel with a solution of water/acetone (15:85 v/v) in a first step and then with water/acetone (60:40). The CLA was finally dried with acetone and then exposed to the air during 24 hours. Other drying procedures (spray-drying, lyophilization) can also be used. The dry polymer was sieved (mesh openings of 75–300 um) and stored at room temperature.

Other CLA polymers with different cross-linking degrees (x) can be obtained in similar conditions, with the mention that the added quantities should be of "x" g epichlorohydrin/100 g of amylose.

A.2. Synthesis of Co-Cross-Linked CL(A-PVA) Polymer Co-Cross-Linked CL(A-PVA)-6 Polymer Synthesis, With Different Ratios A/PVA (3/1; 1/1; 1/3)

The cross-linking degree was maintained constant (clx=6) and different amylose/PVA initial polymer ratios were prepared: A/PVA—(3/1) corresponding to 225 g A/75 g PVA; A/PVA=(1/1) corresponding to 150 g A/150 g PVA; A/PVA—(1/3) corresponding to 75 g A/225 g PVA.

For each synthesis, the required amount of PVA powder (MW 9,000–146,000, 87–89% hydrolysis degree) was suspended in 1 L of 1.5 N sodium hydroxide and heated at 95° C. with strong stirring. After the system became macroscopically homogeneous, the temperature was decreased at 50° C. Separately, for each synthesis, the corresponding amount of high amylose starch (Hylon VII) was suspended in 750 mL cold distilled water in the Hobart® mixer and heated, under stirring, at 50° C. Subsequently, the PVA/NaOH solution was slowly added to the corresponding high amylose starch suspension, under continuous stirring and the system kept for 20 min at controlled temperature (50–55° C.) for high amylose starch gelatinization.

a) Synthesis of CL(A-PVA)-6 With Epichlorohydrin As Cross-Linking Agent

For each gelatinized batch (at 40–60° C.), an amount of 18 g epichlorohydrin (clx=6) was added. After 1 hour at 50° C., the mixture was neutralized with 0.75 M acetic acid solution, and then washed and dried with acetone. Other drying procedures (spray-drying, lyophilization) can also be used. The powders were sieved and kept in dark bottles at room temperature.

b) Synthesis of CL(A-PVA)-6 With Sodium-Trimetaphosphate (STMP) as Cross-Linking Agent The gelatinized batch, was treated with an amount of 18 g STMP. After 1 h at 50° C., the mixture was neutralized with 0.75 M acetic acid solution, and then washed and dried with acetone. Other drying procedures (spray-drying, lyophilization) can also be used. The powders were sieved and kept in dark bottles at room temperature.

B. Drug release in vitro

Example 1:

10% acetaminophen tablets

CLA (x=3.25) 90%

Acetaminophen 10%

Method

The CLA used in this example was cross-linked with sodium trimetaphosphate. The drug was mixed with CLA in a bag for 2–3 minutes and the blend was compressed using a tablet press with round 5/16 inch toolings. The weight of the tablets was 200 mg.

Example 2:

10% pseudoephedrine tablets

CLA (x=3.25) 90%

Pseudoephedrine HCl 10%

Methods

The CLA used in this example was cross-linked with sodium trimetaphosphate. The drug was mixed with CLA in a bag for 2–3 minutes and the blend was compressed using a tablet press with round 15/32 inch toolings. The weight of the tablets was 500 mg.

Test Procedure

The dissolution release profile of the tablets was determined using a USP type III dissolution apparatus. The dissolution system was set up with different dissolution fluids that mimic the GI tract environment with or without enzyme (4500 I.U./L). One international unit (I.U.) will liberate 1 mg of maltose from starch in three minutes at pH 6.9 at 20° C. The drug release was recorded spectrophotometrically with an automated sampling system.

We claim:

1. A solid controlled release oral pharmaceutical dosage unit in the form of a tablet comprising a blend of 0.01–80% by weight of the tablet of a dry powder of a pharmaceutical product, and 20–99.99% by weight of the tablet of a dry powder of high amylose starch, wherein said high amylose starch comprises a mixture of from about 10–60% by weight of amylopectin and from about 40–90% amylose, wherein said high amylose starch has been covalently cross-linked with a covalent cross-linking agent wherein the cross-linking has been carried out with from about 0.1 g to about 30 grams of cross-linking agent per 100 g of said high amylose starch, wherein said dosage unit is resistant to degradation by amylase.

2. A solid controlled release pharmaceutical dosage unit according to claim 1, wherein said covalent cross-linking agent is 2,3-dibromopropanol, epichlorohydrin, sodium trimetaphosphate, linear mixed anhydrides of acetic and di- or tribasic carboxylic acids, vinyl sulfone, diepoxides, cyanuric chloride, hexahydro-1,3,5-trisacryloyl-s-triazine, hexamethylene diisocyanate, toluene 2,4-diisocyanate, N,N-methylenebisacrylamide, N,N'-bis(hydroxymethyl) ethyleneurea, phosgene, tripolyphosphate, mixed carbonic-carboxylic acid anhydrides, imidazolides of carbonic and polybasic carboxylic acids, imidazolium salts of polybasic carboxylic acids, guanidine derivatives of polycarboxylic acids, or esters of propynoic acid.

3. A solid controlled release pharmaceutical dosage unit according to claim 1, wherein said pharmaceutical product is pseudoephedrine hydrochloride.

4. A solid controlled release pharmaceutical dosage unit according to claim 1, wherein said pharmaceutical product is acetaminophen.

5. A solid controlled release pharmaceutical dosage unit according to claim 1, wherein said covalent cross-linking agent is epichlorohydrin.

6. A solid controlled release pharmaceutical dosage unit according to claim 1, wherein said covalent cross-linking agent is sodium trimetaphosphate.

7. The solid controlled release pharmaceutical dosage unit of claim 1 further comprising a polysaccharide or a polyol.

8. The solid controlled release pharmaceutical dosage unit according to claim 7, wherein said polysaccharide is a β-(1–3)glycan, xanthan gum, locust bean gum or guar gum.

9. The solid controlled release pharmaceutical dosage unit according to claim 7, wherein said polyol is polyvinylalcohol.

10. A method for imparting sustained release to a pharmaceutical product, comprising the steps of:
    (a) providing the pharmaceutical product in dry powder form; and
    (b) blending the pharmaceutical product with a powder comprising a high amylose starch, wherein said high amylose starch comprises a mixture of from about 10–60% amylopectin and 40–90% amylose, wherein said high amylose starch has been covalently cross-linked with a cross-linking agent wherein the cross-linking has been carried out with from about 0.1 g to about 30 g of cross-linking agent per 100 g of said high amylose starch; and
    (c) compressing the blend to form a tablet.

11. A method according to claim 10, wherein step (b) comprises mixing the pharmaceutical product in an amount of from 0.01 to 80% by weight of the tablet with a powder comprising cross-linked high amylose starch in an amount of from 20–99.99% by weight of the tablet.

12. A method according to claim 10, wherein the cross-linking agent is sodium trimetaphosphate.

13. A method according to claim 10, where step (b) is carried out with from about 0.1 g to about 30.0 g of sodium trimetaphosphate per 100 g of high amylose starch.

14. A solid controlled release pharmaceutical dosage unit in the form of a tablet comprising:
    (a) a pharmaceutical product;
    (b) high amylose starch, wherein said high amylose starch comprises 10–60% by weight amylopectin and 40–90% by weight amylose; and
    (c) a polysaccharide or a polyol;
wherein said high amylose starch and said polysaccharide or said polyol have been covalently co-cross-linked with a covalent cross-linking agent wherein the cross-linking has been carried out with from about 0.1 g to about 30 g of cross-linking agent per 100 g of high amylose starch.

15. A solid controlled release pharmaceutical dosage unit according to claim 14, wherein said polysaccharide is a β-(1–3)glycan, xanthan gum, locust bean gum or guar gum.

16. A solid controlled release pharmaceutical dosage unit according to claim 14, wherein said polyol is polyvinylalcohol.

17. A solid controlled release pharmaceutical dosage unit according to claim 14, wherein said covalent cross-linking agent is 2,3-dibromopropanol, epichlorohydrin, sodium trimetaphosphate, linear mixed anhydrides of acetic and di- or tribasic carboxylic acids, vinyl sulfone, diepoxides, cyanuric chloride, hexahydro-1,3,5-trisacryloyl-s-triazine, hexamethylene diisocyanate, toluene 2,4-diisocyanate, N,N-methylenebisacrylamide, N,N'-bis(hydroxymethyl) ethyleneurea, phosgene, tripolyphosphate, mixed carbonic-carboxylic acid anhydrides, imidazolides of carbonic and polybasic carboxylic acids, imidazolium salts of polybasic carboxylic acids, guanidine derivatives of polycarboxylic acids, or esters of propynoic acid.

18. A solid controlled release pharmaceutical dosage unit according to claim 14, wherein said pharmaceutical product is pseudoephedrine hydrochloride.

19. A solid controlled release pharmaceutical dosage unit according to claim 14, wherein said pharmaceutical product is acetaminophen.

20. A solid controlled release pharmaceutical dosage unit according to claim 14, wherein said covalent cross-linking agent is epichlorohydrin.

21. A solid controlled release pharmaceutical dosage unit according to claim 14, wherein said covalent cross-linking agent is sodium trimetaphosphate.

22. A method for imparting sustained release to a pharmaceutical product, comprising the steps of:
    (a) providing the pharmaceutical product in dry powder form;
    (b) blending the pharmaceutical product with a powder comprising a high amylose starch, wherein said high amylose starch comprises 10–60% by weight amylopectin and 40–90% by weight amylose, wherein said high amylose starch has been covalently co-cross-linked with a polysaccharide or polyol and a cross-linking agent wherein the cross-linking has been carried out with from about 0.1 g to about 30 g of cross-linking agent per 100 g of said high amylose starch; and
    (c) compressing the blend to form a tablet.

23. A method according to claim 22, wherein step (b) comprises blending said polysaccharide or polyol with high amylose starch prior to cross-linking the high amylose starch.

24. A method according to claim 22, wherein said polyol is polyvinylalcohol.

25. A method according to claim 22, wherein said polysaccharide is a β-(1–3)glycan, xanthan gum, locust bean gum or guar gum.

26. A method according to claim 22, wherein step (b) comprises mixing the pharmaceutical product in an amount of from 0.01 to 80% by weight of the tablet with a powder comprising cross-linked high amylose starch in an amount of from 20–99.99% by weight of the tablet.

27. A method according to claim 22, wherein the cross-linking agent is sodium trimetaphosphate.

28. A method according to claim 22, where step (b) is carried out with from about 0.1 g to about 30.0 g of sodium trimetaphosphate per 100 g of high amylose starch.

29. A method for imparting sustained release to a pharmaceutical product, comprising the steps of:
    (a) providing the pharmaceutical product in dry powder form;
    (b) blending the pharmaceutical product with a powder comprising a high amylose starch, wherein said high amylose starch comprises 10–60% by weight amylopectin and 40–90% by weight amylose, wherein said high amylose starch has been covalently cross-linked using a covalent cross-linking agent wherein the cross-linking has been carried out with from about 0.1 g to about 30 g of cross-linking agent per 100 g of said high amylose starch;

(c) blending the powder of step (b) with a polysaccharide or polyol; and (d) compressing the blend to form a tablet.

30. The method according to claim 29, wherein said polyol is polyvinylalcohol.

31. The method according to claim 29, wherein said polysaccharide is a β-(1–3)glycan, xanthan gum, locust bean gum or guar gum.

32. The method according to claim 29, wherein the cross-linking agent is sodium trimetaphosphate.

33. The method according to claim 29, where step (b) is carried out with from about 0.1 g to about 30.0 g of sodium trimetaphosphate per 100 g of high amylose starch.

34. The method according to claim 33, wherein step (b) comprises mixing the pharmaceutical product in an amount of from 0.01 to 80% by weight of the tablet with a powder comprising cross-linked high amylose starch in an amount of from 20–99.99% by weight of the tablet.

* * * * *